(12) United States Patent
van den Brink et al.

(10) Patent No.: US 7,488,452 B2
(45) Date of Patent: Feb. 10, 2009

(54) SYSTEM FOR PERFORMING EXPERIMENTS, IN PARTICULAR FOR HIGH THROUGHPUT EXPERIMENTATION

(75) Inventors: Peter John van den Brink, Driebergen (NL); Maarten Bracht, Amsterdam (NL)

(73) Assignee: Avantium International B.V., Amsterdam (NL)

( * ) Notice: Subject to any disclaimer, the term of this patent is extended or adjusted under 35 U.S.C. 154(b) by 657 days.

(21) Appl. No.: 10/477,030

(22) PCT Filed: May 13, 2002

(86) PCT No.: PCT/EP02/05323

§ 371 (c)(1),
(2), (4) Date: Apr. 9, 2004

(87) PCT Pub. No.: WO02/092221

PCT Pub. Date: Nov. 21, 2002

(65) Prior Publication Data

US 2004/0156756 A1 Aug. 12, 2004

(30) Foreign Application Priority Data

May 11, 2001 (EP) .................................. 01201738

(51) Int. Cl.
*G01N 21/00* (2006.01)
(52) U.S. Cl. ...................................................... 422/82
(58) Field of Classification Search .................... 422/81
See application file for complete search history.

(56) References Cited

U.S. PATENT DOCUMENTS 3,843,561 A * 10/1974 Sobel ........................... 502/339
5,453,256 A * 9/1995 Rumpf et al. ............... 422/211
6,551,832 B1 * 4/2003 Deves et al. .................. 436/37
6,766,817 B2 7/2004 da Silva

FOREIGN PATENT DOCUMENTS

| DE | 128246 | 8/1900 |
| EP | 1 072 886 A1 | 1/2001 |
| EP | 1072886 A1 * | 1/2001 |

OTHER PUBLICATIONS

Derouane et al.; Combinatorial Catalysis and High Throughput Catalyst Design and Testing; 2000; Kluwer Academic Publishers, Dordrecht, NL XP-002179589; p. 266, figure 14; p. 368, figure 3.
Van Giezen; Chapter 3: Effect of water on the combustion of methane on supported palladium catalysts; 1997, PHD Thesis; The Catalyst Combustion of Methane; XP-002179590; p. 35, paragraph 2.2, p. 36.

* cited by examiner

*Primary Examiner*—Walter D Griffin
*Assistant Examiner*—Bobby Ramdhanie
(74) *Attorney, Agent, or Firm*—Hoffmann & Baron, LLP

(57) ABSTRACT

The system comprises a flow through reaction vessel having an inlet, an outlet and a reaction zone intermediate said inlet and outlet. The system further comprises reagent feed means for introducing one or more reagents into said vessel, said one or more reagents forming one or more reaction products in said reaction zone. Said reagent feed means at least include a liquid feed means for introducing a liquid into said inlet of said vessel. The vessel has a liquid evaporation zone intermediate said inlet and said reaction zone. Said liquid evaporation zone comprises an evaporation structure contacting said liquid and providing a liquid residence time in said liquid evaporation zone improving evaporation of said liquid.

6 Claims, 4 Drawing Sheets

SYSTEM FOR PERFORMING EXPERIMENTS, IN PARTICULAR FOR HIGH THROUGHPUT EXPERIMENTATION

FIELD OF THE INVENTION

The present invention relates to a system for performing experiments, in particular for high throughput experimentation. The system comprises:
- a flow through reaction vessel having an inlet, an outlet and a reaction zone intermediate said inlet and outlet,
- reagent feed means for introducing one or more reagents into said vessel, said one or more reagents forming one or more reaction products in said reaction zone,
- said reagent feed means at least including a liquid feed means for introducing a liquid into said inlet of said vessel,
- said vessel further having a liquid evaporation zone intermediate said inlet and said reaction zone.

A flow through reaction vessel is used for performing chemical and/or physical reactions in a reaction zone in said vessel. To that end one or more reagents are fed into the vessel to react in said reaction zone to form one or more reaction products.

BACKGROUND OF THE INVENTION

In high throughput experimentation a large number of experiments are carried out in parallel in order, for instance, to determine optimal process conditions.

A problem which occurs when using known systems is that unevaporated liquid reagent can be swept undesirable into a heated or hot reaction zone and flash boil. If a gaseous reagent is also fed to the reaction zone said liquid could be entrained by the gas aggravating said problem even further. Also, due to surface tension effects, droplets may be formed on the inner wall of the vessel, which droplets are difficult to heat and will thus not evaporate properly, result in droplets of reagent reaching the reaction zone, which leads to a fluctuating feed of liquid reagent to the reaction zone. This impairs control of the circumstances and reactions(s) in the reaction zone, resulting in undesired variations in pressure, temperature, concentration of reagents, etc. Also this impaired control may lead to unwanted by-products in a reaction.

The above mentioned problem is particularly pertinent in the case of small volume vessels, as is the case in high throughput experimentation. In these experiments a small amount of liquid reagent is fed to the reaction zone, possibly in combination with a gaseous reagent, and consequently relatively minor evaporation rate changes of the liquid reagent will have influence on partial pressures in the reaction zone which impair the reaction performance and results obtained.

The known system are also unsatisfactory in trickle flow experiments, where it is desired that a part of the liquid reagent is evaporated and is in equilibrium with a gaseous reagent feed to the reaction zone, whereas another part of the liquid should reach the reaction zone in liquid phase. These experiments too require a uniform and stable evaporation rate not achieved by the prior art systems.

OBJECT OF THE INVENTION

It is an object of the present invention to overcome the above problem, in particular in the field of high throughput experimentation.

It is a further object of the present invention to provide alternative reaction vessels, as well as systems for high throughput experimentation.

SUMMARY OF THE INVENTION

The first mentioned object is achieved by a system for performing experiments, in particular for high throughput experimentation, said system comprising:
- a flow through reaction vessel having an inlet, an outlet and a reaction zone intermediate said inlet and outlet,
- reagent feed means for introducing one or more reagents into said vessel, said one or more reagents forming one or more reaction products in said reaction zone,
- said reagent feed means at least including a liquid feed means for introducing a liquid into said inlet of said vessel,
- said vessel further having a liquid evaporation zone intermediate said inlet and said reaction zone. In this system said liquid evaporation zone comprises an evaporation structure contacting said liquid and providing a liquid residence time in said liquid evaporation zone improving evaporation of said liquid.

The system according to the present invention provides for an improved or enhanced evaporation of the liquid reagent, while it is prevented that the liquid feed is swept into the reaction zone and/or entrained in a gas flow, if present. Herewith an excellent control and stability of the conditions in the reaction zone is possible.

The invention provides a controlled evaporation of the liquid, in particular a stable non-fluctuating evaporation rate of the liquid reagent. In this respect it is noted that the evaporation does preferably not result from heating the liquid to its boiling point (as such evaporation cannot be easily controlled). In the system according to the invention, the liquid is preferably evaporated at a temperature below the boiling point of the liquid. If desired, the evaporated liquid may of course be further heated to a temperature far above the boiling point before or as it reaches the reaction zone.

According to the present invention, with "reaction zone" any zone (e.g. a reaction zone having a catalyst bed) in the vessel is meant which involves a reaction resulting in e.g. a chemical and/or physical change of matter.

In an advantageous embodiment the system comprises a liquid feed conduit having a mouth closely adjacent the evaporation structure, preferably within 5 millimetres, more preferably within 1 millimetre, most preferably within 0.5 millimetre.

In a further preferred embodiment the system comprises a liquid feed conduit having a mouth contacting the evaporation structure and/or lying within said evaporation structure.

In a preferred embodiment, in particular for high throughput experimentation, the liquid feed conduit is a capillary.

It is preferred that the evaporating structure extends over the entire distance between the mouth of the liquid feed conduit and the reaction zone.

Preferably the vessel is a tubular vessel having an inlet and outlet at opposite ends thereof e.g. a glass-, stainless steel or quartz tube.

In a practical embodiment the vessel is arranged such that said inlet is arranged above said outlet and said evaporation zone is located above said reaction zone. In this orientation of the vessel a preferred embodiment of the evaporation structure provides a capillary force counteracting at least partly gravity acting on the liquid, thereby increasing the liquid residence time of unevaporated liquid in said evaporation zone.

In a preferred embodiment the evaporation structure is porous structure, which could in a preferred embodiment provide the capillary force.

Such a porous evaporation structure could comprise a bed of particles of a non-porous material, e.g. a packed bed of solid grains having a high wettability, especially in cases that the affinity of the liquid to the solid grains is high.

As an alternative a bed of particles of a porous material can be used as evaporation structure, e.g. a packed bed of open porous grains (e.g. porous alumina or silica)

Preferably the porous evaporation structure has a heterogeneous pore distribution.

In a further embodiment the porous evaporation structure comprises a fibrous material. Preferably the porous evaporation structure comprises a woven or braided fibrous material, such as e.g. cloth, felt, glass braid.

The fibrous material may be used as evaporation structure providing a capillary effect. A suitable glass braid material is supplied by Merrem ODS B. V., Zaltbommel, The Netherlands, product nrs. 09020100 and 09020050.

In yet another embodiment the porous evaporation structure comprises a foam body, preferably a metallic or ceramic foam.

If the evaporation structure is made from an open porous material, in particular having a heterogeneous pore distribution, the liquid to be fed to the reaction zone can be retained in the evaporation structure when in liquid phase and can pass when evaporated. Herewith, the smaller pores of the porous material provide for the capillary force to retain unevaporated liquid in the evaporation zone while the evaporated liquid, in the form of vapour or gas, can pass through the bigger pores of the porous material. The person skilled in the art will understand that no general magnitudes for the pores can be given. The smaller pores of the porous material should therefore be small enough to generate sufficient capillary rising to moderate any uncontrolled motion of the liquid. As water has a higher surface tension than acetone, the respective pores have to be smaller for acetone than for water. For example, for water a pore size <0.1 mm and for acetone a pore size of <0.03 mm may be used. If a porous material having a heterogeneous pore distribution is used, it is preferred that the bigger pores are at least two times as big as the smaller pores.

According to a further preferred embodiment, the pore distribution in the porous material of the evaporation structure is such that "liquid jumps" in the evaporation structure are prevented. This means that in the porous material there should be preferably no large segments present that contain only relative large pores resulting in the movement of the liquid throughout the structure being determined by Haines jumps, leading to a fluctuating evaporation.

Alternatively, no "liquid jumps", will occur if an interconnected zone of small pores is present in the porous material that runs all the way from the begin portion (i.e. where the liquid enters) of the evaporation structure to the end portion thereof.

In an advantageous embodiment of the system the reagent feed means further comprise a gas feed means for introducing a gas into said vessel, and the evaporation structure allows the flow of said gas through said evaporation zone so that said gas reaches the reaction zone. The gas could be introduced upstream of the evaporation structure, e.g. in the inlet of the vessel. It is however also conceivable that the gas is introduced downstream of the evaporation structure, in between the structure and the reaction zone.

If the evaporation structure is a porous structure a preferred embodiment provides that said porous evaporation structure extends across the cross-section of the vessel, the porosity of the evaporation structure allowing the passage of gas through said evaporation structure.

In another embodiment the evaporation structure has a body having one or more gas passages for allowing the passage of said gas. In a practical embodiment the evaporation structure has an essentially annular body having a central gas passage. Preferably the gas passages have a diameter of less than 2 centimetre, more preferable less than 1 centimetre, most preferable less than 0.5 centimetre.

In a possible design the body having one or more gas passages could be a porous body. Herewith it can be ensured that the liquid to be fed to the reaction zone can be retained in the porous material of the body when in liquid phase and can be passed via the one or more gas passages when evaporated. The gas stream fed to the reaction zone will flow substantially through the gas passages. In this respect it is noticed that the one or more through going gas passages or channels are present in addition to optional passages or channels present in the evaporation structure itself (e.g. in the porous material).

Preferably the actual capacity of the porous evaporation structure to absorb liquid is limited, so that the liquid is not absorbed too long. It is preferred that the ratio between absorption capacity (ml) and liquid feed (ml/min) is less than 100 (min), more preferably less than 50 (min), most preferably less than 20 (min).

In a practical embodiment the evaporation structure comprises a helical formation on an inner wall of said vessel, e.g. a screwthreaded part of said inner wall or a coil mounted in said vessel and contacting the inner wall of said vessel. Possibly the coil is made from a porous material or has a rough and wettable surface.

Preferably the material of the evaporation structure has a contacting angle of less than 90° with the liquid. This means that the liquid has a propensity to wet the surface of the material. This provides for a good wettability of the evaporation structure and therefore results in an effective retention of liquid until it is suitably evaporated.

In another preferred embodiment the evaporation structure is formed as a coating on at least a part of the inner wall of the vessel, preferably an open porous coating. Herewith a very efficient and simple retention of unevaporated liquid can be achieved, while liquid in vapour or gas form can pass the evaporation zone. The porous material may have a homogeneous or heterogeneous pore distribution, as long as a sufficient retention of the unevaporated liquid is secured.

In another preferred embodiment the evaporation structure is formed as a roughened surface of at least a part of the inner wall of the vessel, formed for instance by mechanical of chemical means.

In an advantageous design of the vessel the evaporation structure adjoins the reaction zone.

In a practical embodiment the evaporation structure extends over a segment of the circumference of the inner wall of the vessel, the remainder of the circumference being formed by the inner wall of the vessel.

In a practical embodiment the evaporation structure is removably mounted in the vessel.

In a preferred embodiment the reaction zone comprises catalyst, e.g. a heterogeneous catalyst.

Preferably the vessel has a vessel wall made of a heat conducting material, preferably a metal. This embodiment allows for instance that heat is transferred from said reaction zone to said evaporation zone assisting the evaporation of said liquid.

In a preferred embodiment the system further comprises a controllable heat exchange means for controlling the temperature of the evaporation zone, in particular the evaporation structure.

In a further detailed embodiment thereof the heat exchange means comprise a heating means, preferably adapted to provide a temperature gradient over said evaporation zone having an increasing temperature in the direction to the reaction zone.

In a preferred embodiment cooling means are provided for cooling in the region of the inlet of the vessel, preferably in the region of the mouth of a liquid feed conduit. The cooling provides for a desirable temperature gradient which results in an evaporation without boiling and prevents boiling of the liquid in the liquid feed conduit (which is desirable for liquid having a low boiling temperature).

In an advantageous embodiment, in particular for high throughput experimentation, the system further comprises a housing having at least vessel receiving bore for removable housing the vessel. In particular it is preferred that the housing comprises multiple vessel receiving bores, e.g. 8, 16, 32, 64 or 96, each receiving a vessel.

In a practical embodiment each vessel receiving bore is arranged vertically in the housing. It is then advantageous if the vessel receiving bore has an opening for insertion and removal of the vessel at the top.

In a further preferred embodiment of said system having a housing for removable housing said vessel, the system also has a liquid feed channel in communication with said inlet of said vessel for feeding a liquid reagent into said vessel, a gaseous reagent feed channel in communication with said inlet of said vessel for feeding a gaseous reagent into said vessel, and an outlet channel in communication with said outlet of said vessel for removal of said reaction product(s), said system further including a transfer fluid feed channel in communication with said outlet channel for feeding a transfer fluid into said outlet channel, said transfer fluid facilitating the transfer of said reaction product(s).

In an advantageous embodiment of the above system said reaction product is a gaseous reaction product and said transfer fluid is a transfer gas, preferably an inert gas, adapted to prevent condensation of said gaseous reaction product. Preferably this system comprises heating means for heating said transfer gas and/or said mixture of transfer gas and gaseous reaction product.

In a preferred embodiment said housing comprises a base and a cover, said vessel receiving bore being formed in said base and having an opening allowing insertion and removal of said vessel at a first face of said base, said cover being removably mountable on said first face to cover said opening of said bore, said liquid and gaseous reagent feed channels being provided in said cover and/or said base communicating with said inlet of said vessel, wherein a sealing means is provided between said vessel and said bore preventing the bypassing of reagent between the vessel and the base.

It is preferred that an annular gap is present between said vessel and said vessel receiving bore, said sealing means prevent reagent flow along said gap to the outlet of said vessel, and said transfer fluid channel opening into said annular gap between said sealing means and said outlet of said vessel.

In a further preferred embodiment said reaction zone is located between said sealing means and said outlet of said vessel, and a reaction zone heating means for heating said reaction zone is provided.

In a further preferred embodiment said reaction zone heating means is arranged in said housing and said transfer fluid flows past said reaction zone heating means.

In a practical design said outlet channel extends between the end of said vessel receiving bore remote from the first face and a second face opposite from said first face.

Preferably said outlet channel extends coaxially in line with said vessel receiving bore, and has a diameter smaller than said vessel receiving bore, a support shoulder being present between said vessel receiving bore and said outlet channel supporting said vessel.

The present invention also relates to a vessel.

The present invention also relates to a method for performing experiments, wherein use is made of a system according to the invention.

In a possible embodiment multiple liquid reagents are fed into the vessel and the vessel has an evaporation structure for each liquid.

The system can be used advantageously when the experiments are trickle flow experiments.

The invention also relates to the use of a vessel or system according to the invention in high throughput experimentation.

Hereinafter, the present invention will be illustrated in more detail referring to the drawings.

DETAILED DESCRIPTION OF THE INVENTION

Figure 1:
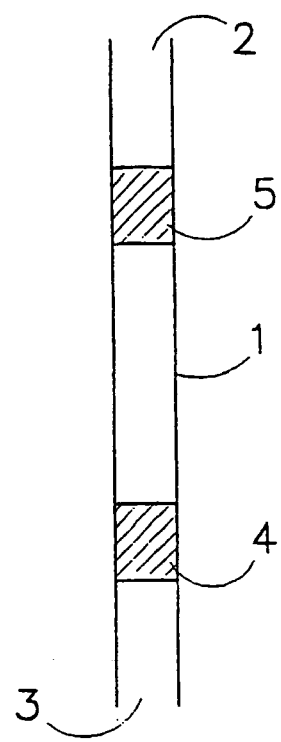
FIG. 1 shows a schematic cross-sectional view of a flow through reaction vessel of a system according to the present invention.

FIG. 1 shows a schematic cross-sectional view of a flow through reaction vessel 1 for use in a system according to the present invention. The vessel 1 has an elongated tubular wall having an inlet 2 and outlet 3 at opposite ends thereof. In the lower part of the vessel 1 a reaction zone 4 is present, such as a reaction zone comprising a catalyst bed, intermediate the inlet 2 and outlet 3.

The vessel 1 also has a liquid evaporation zone 5 intermediate the inlet 2 and the reaction zone 4. The liquid evaporation zone 5 contains an evaporation structure (see e.g. FIGS. 2a,b,c) such that the liquid is evaporated.

In most cases, in evaporation of that liquid, the vapour pressure will be at least equilibrated with the gas pressure.

The evaporation structure is designed such that it can retain substantially all unevaporated liquid fed into the inlet 2 until evaporated, while evaporated liquid is allowed to pass the zone 5 to enter the reaction zone 4.

The person skilled in the art will understand that the evaporation structure in the zone 5 may have a variety of forms, and may be made from a broad range of materials. The person skilled in the art will choose the appropriate form and materials depending on the liquid to be fed, and further conditions which differ from case to case.

Furthermore, the person skilled in the art will understand that the inlet 2 of the vessel 1 may be constructed such as to provide a uniform feed of liquid to the evaporation zone 5. This may be achieved, for instance, by inserting a capillary, thread or tube into the inlet 2 of the vessel 1, and thus by bringing the liquid into direct and continuous contact with the evaporation zone 5.

Figure 2A:
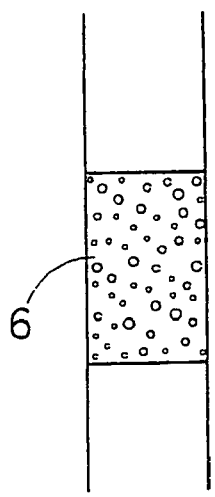
FIGS. 2A, 2B and 2C show schematic magnified cross-sectional views of three alternative evaporation zones for the vessel shown in FIG. 1.
Figure 2B:
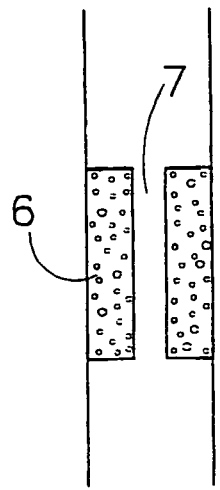
Figure 2C:
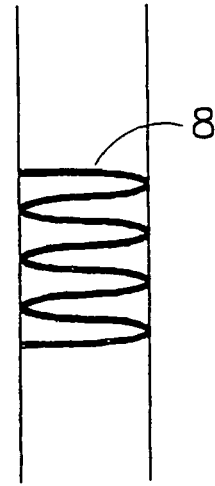

FIGS. 2A, 2B and 2C show three preferred alternative embodiments of the evaporation structure 6 in the zone 5 of the vessel 1 in FIG. 1.

In FIG. 2A the evaporation structure 6 comprises an open porous material having a heterogeneous pore distribution, such that the liquid to be fed to the reaction zone 4 can be retained in the small pores of the structure 6 when in liquid phase, while gases and vapours can pass through the large pores. Preferably the pore distribution in the porous material of the structure 6 is such that blockages and liquid jumps of liquid in the structure 6 are prevented.

FIG. 2B shows an alternative preferred embodiment of the evaporation structure 6. In this embodiment, the wall of the reaction vessel 1 in the zone 5 consists of or is lined with a porous material, optionally in the form of a hose, such as ceramic cloth, felt, glass braid, that acts as a wick and controls the liquid travel trough the evaporation zone 5. The porous material of the evaporation structure 6 may be homogeneous or heterogeneous. A central through going passage 7 is provided for passing the evaporated liquid, and optionally one or more gaseous reagents fed into the inlet 2 of the vessel 1.

FIG. 2C shows another alternative preferred embodiment of the evaporation structure 6. In this embodiment the structure 6 comprises a coil 8. Instead of the coil 8 any other suitable insert may be used. The coil 8, or other suitable insert may be composed of a porous material, or of a non-porous material having a high affinity for the liquid to be fed.

In a simple alternative the evaporation structure 6 is embodied as a screwthreaded part of the inner wall of the vessel 1, preferably extending all the way from the inlet to the reaction zone 4. The liquid will follow the helical path formed by the screwthread and thus have an increased residence time allowing improved evaporation in comparison to a smooth inner wall of the vessel.

In another alternative embodiment the evaporation structure consists of elongated members, such as filaments, wires, rods, strips, etc, extending axially in the evaporation zone of the tubular vessel and having a spacing in between neighbouring members which allows the liquid to remain in between those members under capillary action until evaporated. For instance the evaporation structure consists of a pack of interspaced thin metal rods.

In general, the material used in the structure 6 of FIGS. 2A, 2B and 2C preferably has some affinity to the liquid fed. Preferably the material should have a contact angle of less than 90° to ensure that the material is easily wetted by the liquid. If a heterogeneous material is used, it is preferred that the relatively larger pores do not have a pore size exceeding twice the average of the pore size of all the pores.

The person skilled in the art will understand that, in addition to the embodiments shown in FIGS. 2A-2C, any other suitable embodiment of the structure 6 may be used, for example a grid or rough wall.

In use of the vessel 1 as shown in FIG. 1, a liquid, which may be part of a gas-liquid stream, will be fed in the inlet 2. When entering the zone 5, the gas or vapour part of the stream, or the suitably evaporated liquid, will pass the zone 5 comprising the structure 6 and enter the reaction zone 4.

Advantageously the zone 5 and the structure 6 therein is in direct contact with the reaction zone 4 as is the case in trickle flow. A heating means may be provided in or next to the zone 5, or the wall of the reaction vessel 1 may act as such. After evaporation of the liquid the conditioned stream will pass the zone 5 and enter the reaction zone 4.

EXAMPLE

A vessel made of a stainless steel tube (30 cm, internal diameter 2 mm) was filled with a glass braid of about 20 cm (internal diameter 1.0 mm; supplied by Merrem ODS B. V., Zaltbommel, The Netherlands, product nr. 09020100). The vessel was supplied with a gas flow (10 ml/min) of helium (300° C.). Using a capillary, 2 µl/min water (25° C.) was dripped on the glass braid. The glass braid in the vessel provided for a smooth evaporation of the water, wherein no unconditioned liquid was entrained in the gas flow. Downstream of the glass braid the physical conditions could be maintained substantially uniform during the feeding of liquid.

Figure 3:
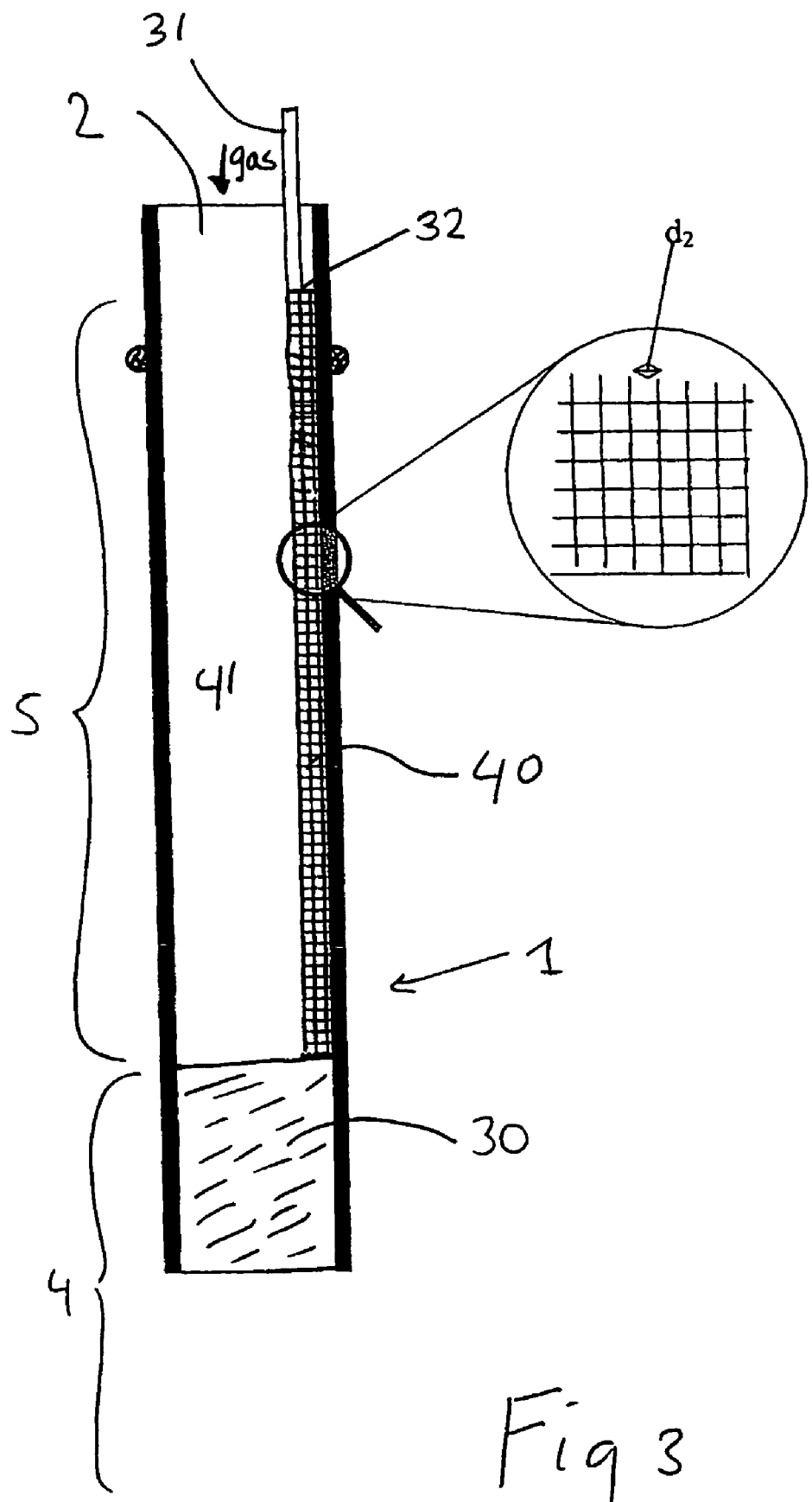
FIG. 3 shows a schematic view of an alternative embodiment of the vessel of a system according to the invention.

In FIG. 3 a part of a tubular vessel 1 is shown adapted for use in high throughput experimentation. The vessel 1 has an inner diameter of several millimetres, preferably less than 20 millimetres, most preferably between 1 and 5 millimetres. The axial length of the vessel 1 preferably is at least 2 centimetres, more preferably more than 10 centimetres, most preferably between 15 and 40 centimetres.

The vessel 1 shown in the example of FIG. 3 has an inner diameter of 2 millimetres and a length of 30 centimetres.

The vessel 1 has an inlet 2 and at the opposite end an outlet (not shown). The vessel 1 is intended for use in a vertical orientation, with the inlet 2 at the top.

The lower part of the vessel 1 contains a reaction zone 4, in this example a catalyst bed 30. The evaporation zone 5 is located above the catalyst bed 30.

A liquid feed conduit 31 in the form of a capillary provides the feed of a liquid reagent into the vessel 1. In high throughput experimentation flow rates of such a liquid feed are very small, sometimes between 1 and 100 microliters per minute.

A gas feed also is introduced into the inlet 2 of the vessel 1, e.g. at a rate of between 1 and 100 ml per minute.

The evaporation zone 5 contains an evaporation structure 40, which extends the full axial length between the mouth 32 of the capillary 31 and the reaction zone 4.

The evaporation structure 6 is formed here as a strip of glass braid contacting the wall of the vessel 1 so that the structure 40 does not extend across the diameter of the vessel and leaves a gas passage 41 for the gas and vapour. As an alternative a hose of glass braid is practical. The pore size (d2) of the pores within the braid preferably is less than 0.2 millimetres, more preferred less than 0.05 millimetres. Preferably the diameter of the gas passage 41 is at least the same as the pore size, more preferably at least twice the pore size. In a preferred embodiment of the vessel the gas passage has at least a diameter of 0.1 millimetre, more preferably at least 0.5 millimetre, most preferably at least 1 millimetre.

Preferably the glass braid 40 is removable from the vessel 1.

The mouth 32 of the capillary is in contact with the evaporation structure 40, which ensure a uniform and continuous flow of liquid reagent into the evaporation structure.

Figure 5A:
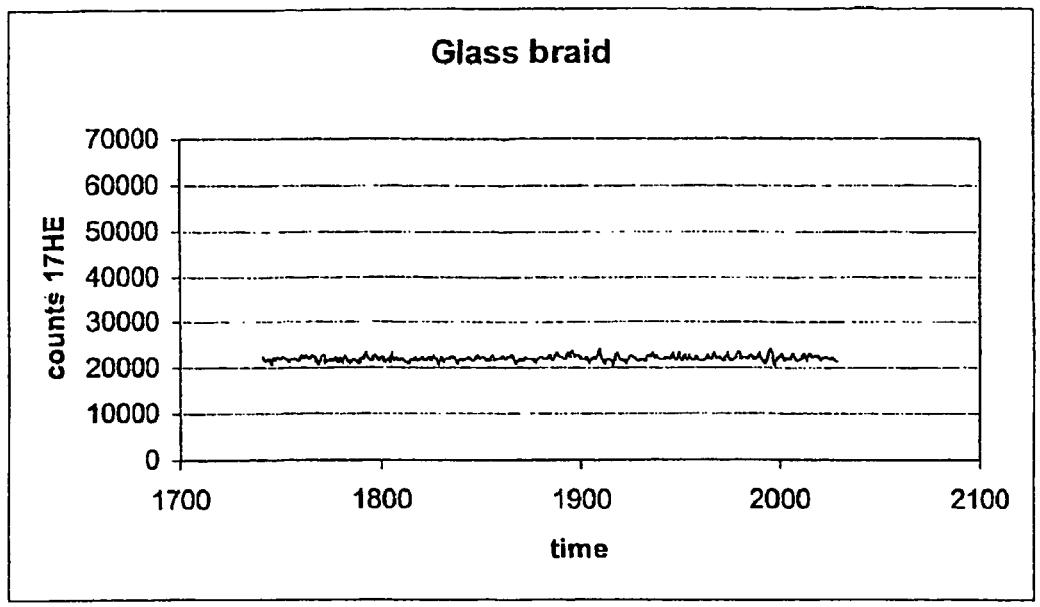
FIGS. 5a and 5b are graphs showing the effect of the liquid conduit contacting or not contacting an evaporation structure of glass braid in a vessel of a system according to the invention.
Figure 5B:
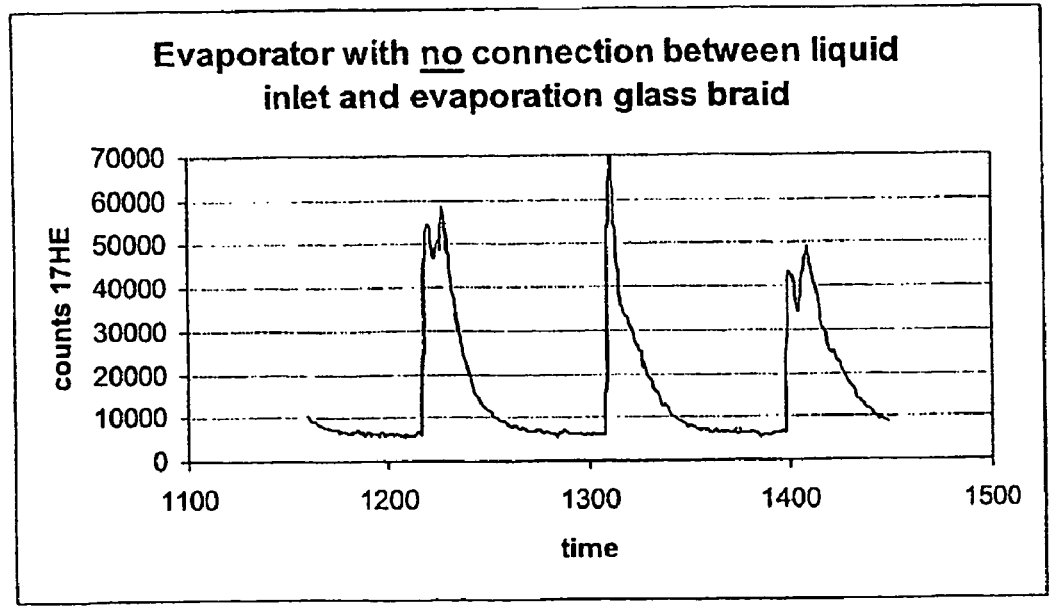

In FIG. 5 the effect of the contact or non contact between mouth 32 of the capillary and evaporation structure 40 is illustrated. In the experiments of FIG. 5 the vessel 1 was supplied with 10 ml/min of a gas and 2 microliter/min of a liquid. The concentration of evaporated liquid (water in this experiment) was measured over time. FIG. 5*a* shows a very uniform concentration indicating a very uniform feed and evaporation of the liquid. In the experiment of FIG. 5*b* a gap was maintained between the mouth of the capillary and the evaporation structure 40. This resulted in an irregular feed and evaporation of the liquid, severely impairing the conditions in the reaction zone 4. Presumably the formation of droplets at the mouth 32 of the capillary 31 are responsible for the observed irregularities in FIG. 5*b*.

Figure 4:
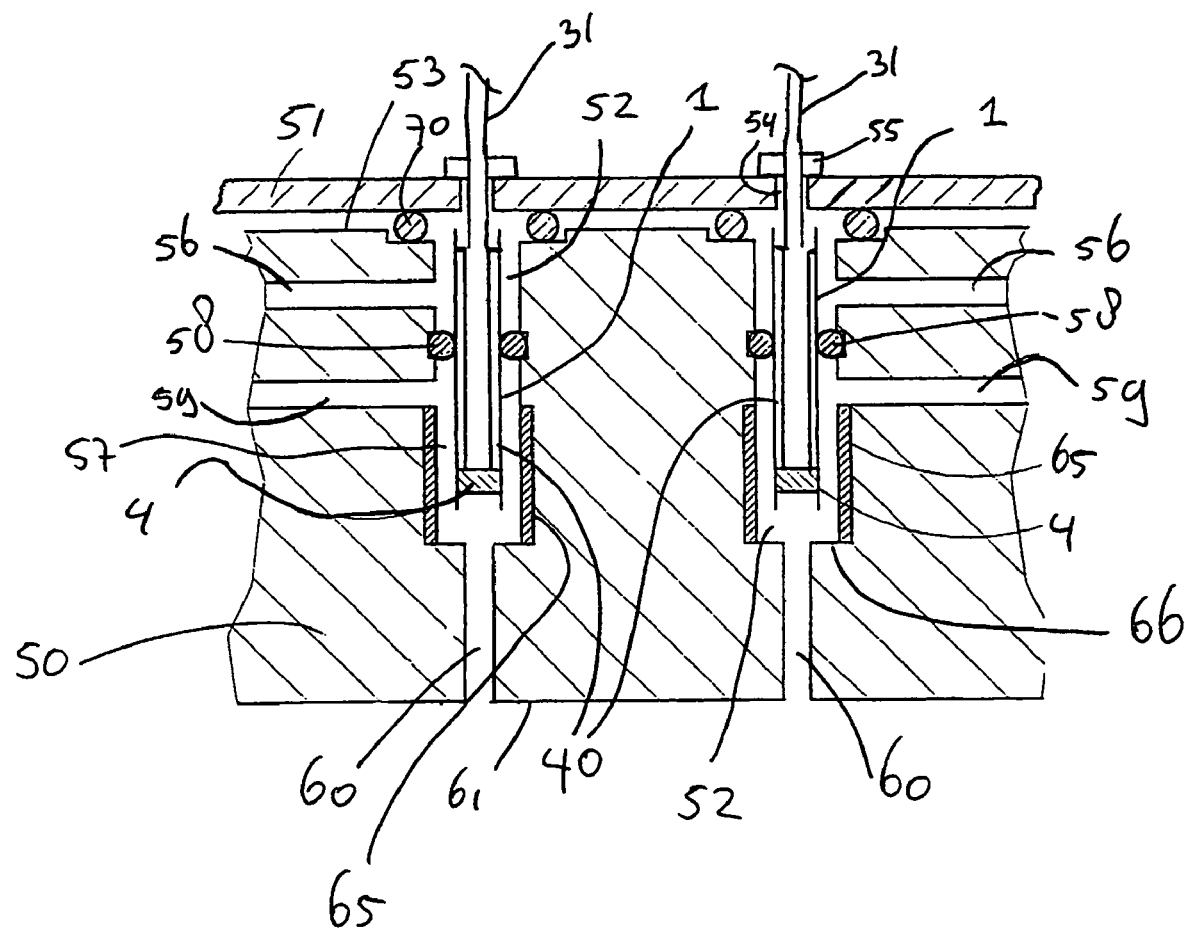
FIG. 4 shows a schematic cross-section of a system according to the invention.

FIG. 4 shows schematically a system according to the invention, primarily designed for high throughput experimentation.

The system comprises a housing having a base 50 and a cover 51. The base 50 is formed here as a solid block having multiple vessel receiving bores 52 formed in said base 50. In each bore 52 a vessel 1 can be inserted and removed via an opening of said bore 52 in the top face 53 of the base 50.

The cover 51 is removably mountable on said top face 53 to cover said openings of the bores 52, so that a chamber is formed in said housing for each vessel. A sealing ring 70 is placed around the top opening of the bore 52 between the top face 53 and the cover 51.

The vessels shown in FIG. 4 are basically of the same design as the vessel 1 in FIG. 3, however the evaporation structure 40 is of an annular design having a central gas and vapour passage.

For feeding a liquid reagent into the inlet of the vessel 1 a capillary 31 extends through a hole 54 in cover 51, sealed by sealing means 55.

For feeding a gaseous reagent into the vessel 1 a gas feed channel 56 is formed in the base 50 communicating with said inlet of said vessel.

As can be seen in FIG. 4 an annular gap 57 is present between the vessel 1 and the vessel receiving bore 52.

In order to avoid a bypass flow of reagent via this gap 57 along the outside of the vessel 1 a sealing means 58 is present. The sealing means 58 could be a sealing ring mounted on the vessel 1.

In FIG. 4 a transfer fluid feed channel 59 is shown for each vessel receiving bore 52, which channel 59 opens into said annular gap between said sealing means 58 and the outlet at the bottom end of the vessel 1. The transfer fluid is primarily intended to facilitate the transfer of the reaction product(s) to a remote analyser, collection system, etc. Also it is intended to keep condensable components in the gas phase by dilution.

The base 50 also has an outlet channel 60 extending between the lower end of the vessel receiving bore 52 and the bottom face 61 of the base 50.

The reaction zone 4 is located between the sealing means 58 and the outlet of the vessel 1.

A reaction zone heating means 65 is mounted in the base 50 for heating the reaction zone 4. Also a cooling means can be added to the cover 51 or the top part of the base 50 for cooling in the region of the inlet of the vessel. This cooling means can assist in creating the desired temperature gradient across the evaporation structure.

It can be seen that the transfer fluid flows past said reaction zone heating means 65.

In FIG. 4 it can be seen that the outlet channel 65 extends coaxially in line with said vessel receiving bore 52 and has a diameter smaller than said vessel receiving bore 52, a support shoulder 66 being present between said vessel receiving bore and said outlet channel supporting said vessel. The vessel 1 could stand on this support shoulder with its lower end.

In a preferred embodiment the reaction product is a gaseous reaction product and the transfer fluid is a transfer gas, preferably an inert gas, adapted to prevent condensation of said gaseous reaction product.

As an alternative or in combination with the reaction zone heating means 65 the system could further comprise heating means, possibly downstream of the outlet channel, for heating the transfer gas and/or said mixture of transfer gas and gaseous reaction product.

Using the system and vessel according to the present invention, substantially no unevaporated liquid will be entrained in the gas flow entering the reaction zone. Also no difficult to heat droplets will be formed due to surface tension effects. Therefore, the vessel allows improved controlling of the conditions in the reaction zone.

It is noted that the liquid introduced into the vessel can also be a mixture of different liquids fed into the vessel via one or more liquid feed conduits.

In an embodiment not shown in the drawings two liquid reagents are fed into the inlet of the vessel 1, for example water and an organic liquid (not soluble in water). It is then proposed to provide two evaporation structures in the vessel, one for the water and one for the organic liquid. In particular each structure has optimal wettability for the corresponding liquid.

The system according to the invention is advantageous for performing trickle flow experiments, where it is desired that a part of the liquid reagent is evaporated and is in equilibrium with a gaseous reagent feed to the reaction zone, whereas another part of the liquid should reach the reaction zone in liquid phase. In particular the system allows to preform these experiments with mixtures of liquids having different boiling temperatures.

In the drawings the vessel 1 is an elongated tubular vessel having a straight tubular wall. However it is also conceivable that the tubular vessel is U-shaped. In one embodiment thereof the evaporation structure and the reaction zone are present in one leg of the vessel, said leg having an inlet at the top thereof so that said evaporation structure is above said reaction zone. The other leg then serves as an outlet channel for the reaction product(s).

The invention claimed is:

1. A system for performing experiments, in particular for high throughput experimentation, said system comprising:
    a flow through reaction vessel having an inlet, an outlet and a reaction zone intermediate said inlet and outlet,
    reagent feed means for introducing one or more reagents into said vessel, said one or more reagents forming one or more reaction products in said reaction zone,
    said reagent feed means at least including a liquid feed means for introducing a liquid into said inlet of said vessel,
    said vessel further having a liquid evaporation zone intermediate said inlet and said reaction zone,
    wherein said liquid evaporation zone comprises an evaporation structure contacting said liquid and providing a liquid residence time in said liquid evaporation zone improving evaporation of said liquid which evaporation structure has a begin portion where the liquid enters the evaporation structure and an end portion where the evaporated liquid leaves the evaporation structure,
    wherein said evaporation structure is a porous structure in which an interconnected zone of small pores is present that runs all the way from the begin portion of the evaporation structure to the end portion thereof,
    and in that the liquid feed conduit has a mouth that is arranged within about 5 millimeters from the evaporation structure.

2. A system according to claim 1, wherein said evaporation structure is porous structure selected from the group of: a bed of particles of a non-porous material, a bed of particles of a porous material, a fibrous material, a woven fibrous material, a braided fibrous material, a foam body, a metallic foam body, a porous coating on an inner wall of the vessel, a coil of porous material mounted in said vessel and contacting an inner wall of said vessel.

3. A system according claim 1, wherein said evaporation structure comprises a helical formation on an inner wall of said vessel.

4. A system according to claim 1, wherein said evaporation structure is formed as a coating on an inner wall of said vessel.

5. A system according to claim 1 which said mouth is arranged with about 1 millimeter from said evaporated structure.

6. A system according to claim 1 wherein said mouth is arranged with 0.5 millimeters from the evaporated structure.

* * * * *